United States Patent [19]

Petersen

[11] Patent Number: 5,129,908
[45] Date of Patent: Jul. 14, 1992

[54] METHOD AND INSTRUMENTS FOR RESECTION OF THE PATELLA

[76] Inventor: Thomas D. Petersen, 9680 Alto Dr., La Mesa, Calif. 92041

[21] Appl. No.: 469,059

[22] Filed: Jan. 23, 1990

[51] Int. Cl.⁵ .............................................. A61B 17/56
[52] U.S. Cl. ...................................... 606/88; 606/86
[58] Field of Search ...................... 606/80, 82, 84, 86, 606/87, 88, 96

[56] References Cited

U.S. PATENT DOCUMENTS

| D. 273,326 | 4/1984 | Peterson et al. | D24/140 |
|---|---|---|---|
| 339,526 | 4/1886 | Butterworth | 606/184 |
| 2,291,413 | 7/1942 | Siebrandt | 606/86 |
| 2,427,128 | 9/1947 | Ettinger | 608/86 |
| 2,698,483 | 1/1955 | Berkowitz | 433/156 |
| 4,312,337 | 2/1982 | Donohue | 606/80 |
| 4,444,180 | 4/1984 | Schneider et al. | 606/96 |
| 4,565,192 | 1/1986 | Shapiro | 606/82 |
| 4,586,497 | 5/1986 | Dapra et al. | 606/80 |
| 4,633,862 | 1/1987 | Petersen | 606/88 |
| 4,706,660 | 11/1987 | Petersen | 606/86 |

FOREIGN PATENT DOCUMENTS

| 0327249 | 8/1989 | European Pat. Off. | |
| 655646 | 5/1986 | Switzerland | 606/86 |
| 1355259 | 11/1987 | U.S.S.R. | 606/86 |

OTHER PUBLICATIONS

Dow Corning Wright Publication titled "We're Pushing all the Wright Buttons".
Richards Catalogue Pages for Patella Reamer Guide and Associated Instruments.
Dow Corning Wright Publication titled "Whiteside Ortholoc II Total Knee System".
Depuy Literature Showing Patellar Clamp and Reamer.
Biomet, Inc. Literature Showing Patellar Instruments.

*Primary Examiner*—Robert A. Hafer
*Assistant Examiner*—Kevin G. Rooney
*Attorney, Agent, or Firm*—H. Jay Spiegel

[57] ABSTRACT

Disclosed is a method of performing surgery to resect the patella for the purpose of installation of a patellar prosthesis, along with instruments used in such surgery. The instruments include a combined clamping device and reaming guide which when clamped about the patella provides a guide for reaming the surface thereof as well as a limit stop device designed to prevent reaming the patella too deeply. The instruments also include a reaming device designed to ream an annulus of material from the patella, leaving a central raised portion for fixation of a patellar prosthesis.

22 Claims, 4 Drawing Sheets

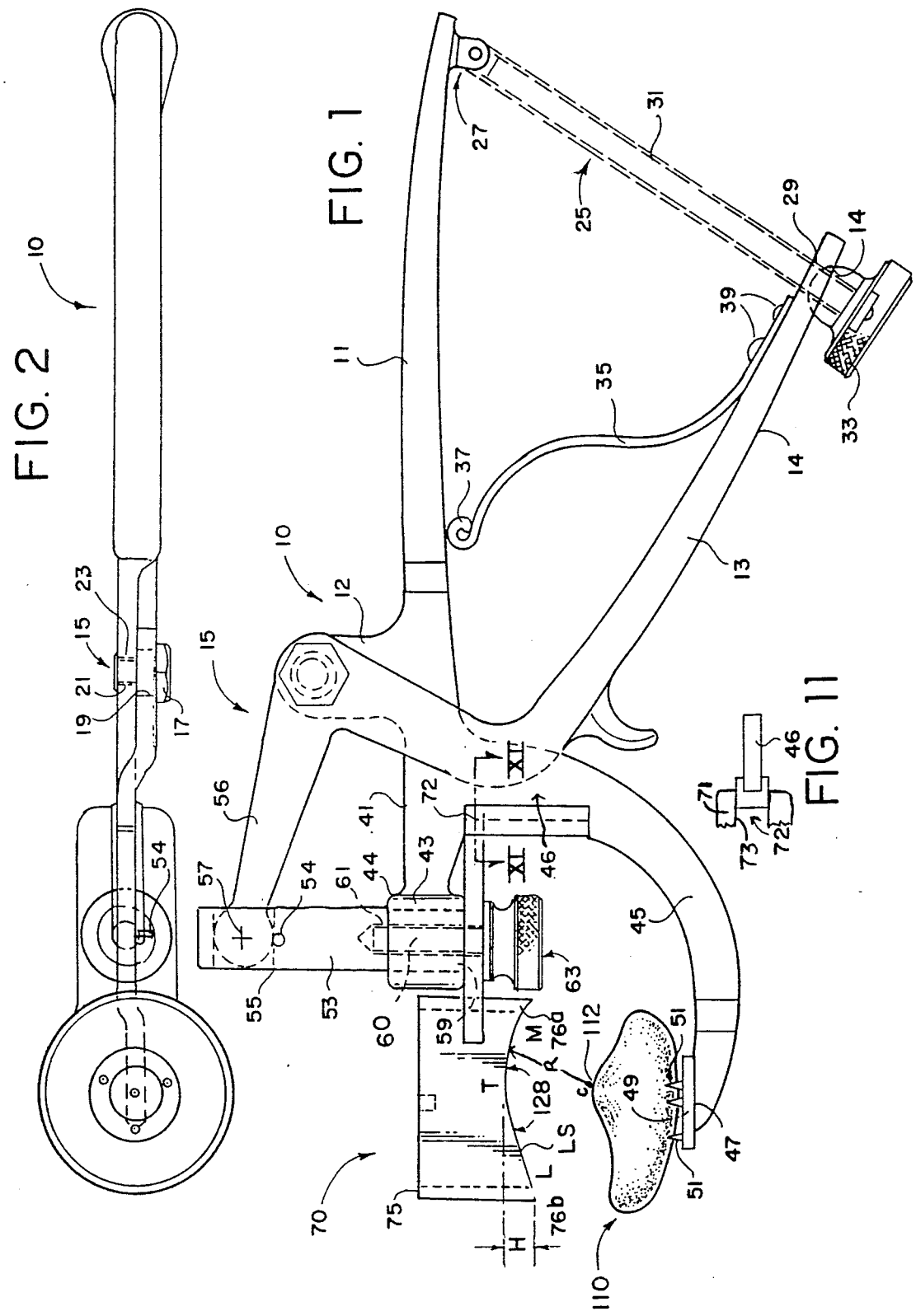

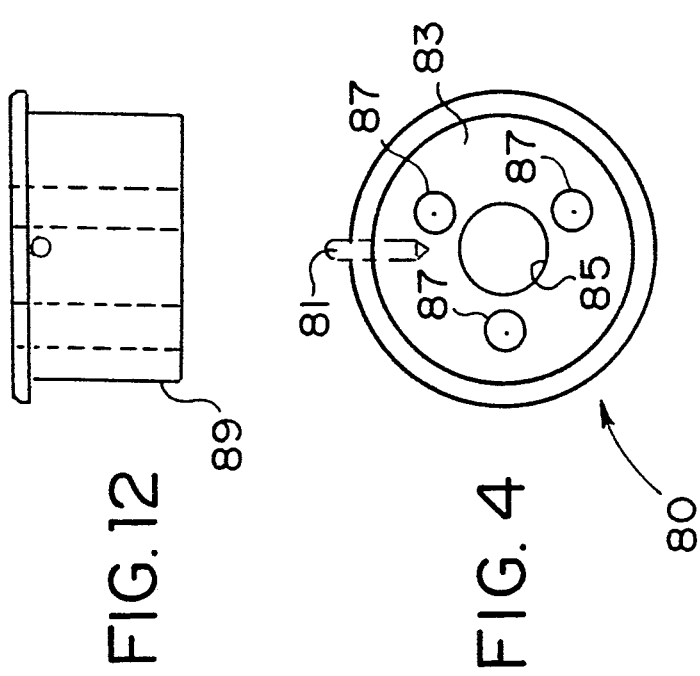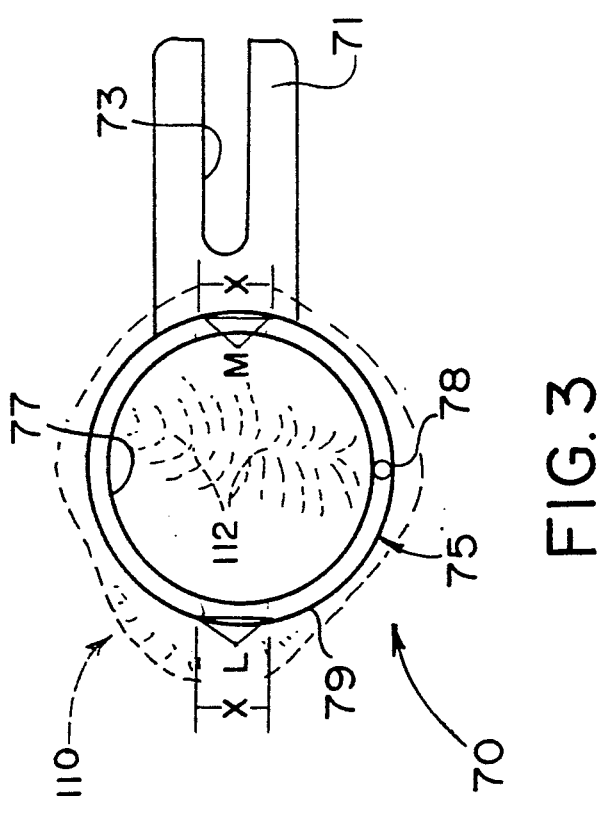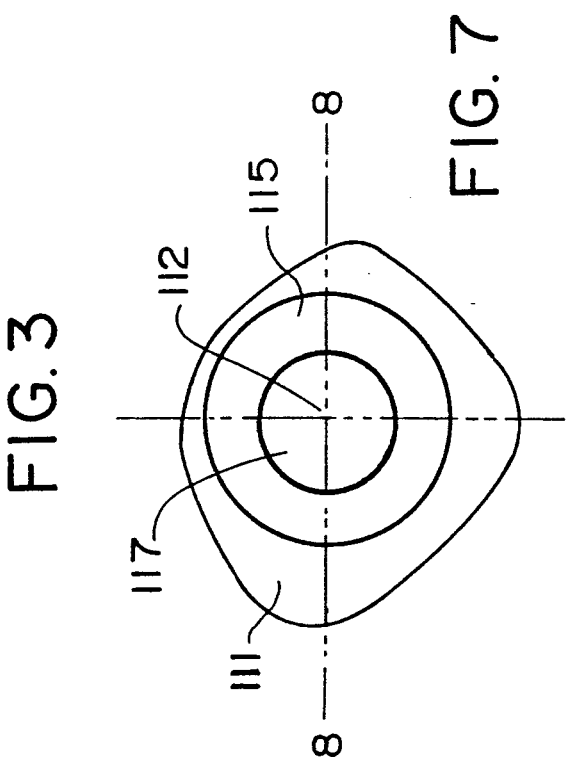

5,129,908

METHOD AND INSTRUMENTS FOR RESECTION OF THE PATELLA

BACKGROUND OF THE INVENTION

The present invention relates to method and instruments for resection of the patella. Applicant has obtained two prior patents disclosing a patellar clamp, U.S. Pat. Nos. 4,706,660 and 4,633,862. These patents are related in that the former-mentioned patent arose out of an application which was a divisional application from the application from which the latter-mentioned United States Patent arose. These patents are incorporated herein by reference along with all prior art cited and discussed during the prosecution thereof.

The patellar clamp disclosed in the two above-mentioned prior United States Patents is designed to be used to install a patellar button prosthesis on a patella which has been predrilled for this purpose. The inventive clamp includes jaws designed to engage anterior and posterior surfaces of the patella to force projections of the patellar button prosthesis into openings preformed in the articular surface thereof. While the mechanism for moving the jaws toward and away from one another is similar in structure to corresponding structure of the present invention, as will be described in greater detail hereinafter, the purposes of the present invention are completely different from those disclosed in the prior patents and the structure for obtaining desired results also differs drastically therefrom.

Of the prior art made of record during the prosecution of the two above-mentioned prior United States Patents, except for those references discussed below, the references are believed to be of only general interest concerning the teachings of the present invention.

U.S. Pat. No. 395,262 to Butterworth discloses a bull ringer including a jaw B having a ring-like termination c designed to engage a portion of the nose of a bull whereupon a jaw C having a cutting punch a extends through the ring c to make an opening through the nose of the bull. The present invention differs from the teachings of Butterworth for reasons including provision of a slideably removable reamer guide device as well as a stop mechanism to limit the depth of reaming of the associated reamer device.

U.S. Pat. No. 4,444,180 to Schneider et al. discloses a clamp-like device wherein one of the jaws thereof comprises a drill guide having a plurality of holes of varying sizes therethrough as shown in FIG. 2 or, alternatively, as including a single large opening as illustrated in FIG. 5. The teachings of Schneider et al. differ from the teachings of the present invention for reasons including, again, removeability of the guide structure as well as a limit stop mechanism to prevent reaming of too much patellar structure.

Again, the references made of record during the prosecution of the above-mentioned prior patents are hereby made of record herein, but are believed to be of only general interest concerning the teachings of the present invention.

SUMMARY OF THE INVENTION

The present invention relates to a method and instruments for resection of the patella articular surface. As stated above, the inventive method is carried out through operation of two instruments, a patellar clamp-guide device and a reaming cutter device, which devices will be described in great detail in the Specific Description of the Preferred Embodiments below.

The present invention includes the following interrelated aspects and features:

(A) In a first aspect, the present invention includes a patellar clamp-guide device including two pivotably mounted structures each of which includes a proximal handle and a distal jaw. These devices are pivotably mounted together at a fulcrum point and the proximal handles are loosely connected together at their proximal ends by a selectively operable locking device. A leaf spring is interconnected between the handles to provide spring bias in direction of separation of the jaws.

One jaw is designed to engage the anterior surface of the patella and includes a plurality of upstanding spikes designed to engage into the anterior surface of the patella. The other jaw includes a selectively detachable reamer guide.

(B) The reamer guide includes a proximal elongated slot designed to be slideably receiveable on the distal end of the second jaw and which may be adjusted in position and orientation and locked into place with a screw fastener. The reamer guide includes a large opening designed to cover a large portion of the articular surface of the patella when the inventive patellar clamp-guide device is clamped thereover. The reamer guide is removeable so that it may be replaced with reamer guides of different sizes to accommodate to patellae of differing sizes and configurations.

(C) The inventive patellar clamp-guide device includes a stop structure designed to prevent the surgeon from reaming too much bone from the patella so that ample bone for fixation remains after the reaming operation has been completed.

(D) The present invention further includes a reaming cutter device including a plurality of blades at the distal end thereof as well as a proximal chuck device designed to attach the reaming cutter device to a rotary reamer. The reaming cutter device itself includes a central portion recessed with respect to an annular outer portion so that when the reaming cutter device is used on a patella, a central raised portion of patella bone remains thereon surrounded by a reamed surface, thus providing a stepped bony structure with significant fixation bone being centrally located on the remaining patella surface. The central bone stabilizes the implanted patellar prosthesis.

(E) The present invention also contemplates a method of surgery carried out in conjunction with the patellar clamp-guide device and reaming cutter device described above. This method will be described in greater detail hereinafter.

As such, it is a first object of the present invention to provide a method and instruments for resection of the patella.

It is a further object of the present invention to provide such instruments to clamp about a patella while guiding reaming of the articular surface thereof.

It is a yet further object of the present invention to provide a reaming cutter device designed to ream bone from the articular surface of the patella while leaving a remaining central raised bony surface for fixation of a patellar button prosthesis.

It is a further object of the present invention to provide a method of performing surgery on the patella for the purpose of installation of a patellar button prosthesis using the instruments described hereinabove.

These and other objects, aspects and features of the present invention will be better understood from the following Specific Description of the Preferred Embodiment when read in conjunction with the appended drawing figures.

BRIEF DESCRIPTION OF THE DRAWINGS

FIG. 1 shows a side view of the patellar clamp-guide device forming a part of the present invention showing a patella positioned for clamping thereby.

FIG. 2 shows a top view of the device illustrated in FIG. 1.

FIG. 3 shows a top view of the reamer guide portion of the device illustrated in FIGS. 1 and 2 as superimposed over a patella.

FIG. 4 shows a drill jig useable with the reamer guide illustrated in FIG. 3.

FIG. 7 shows a view of a patella looking at the articular surface thereof after reaming has taken place.

FIG. 11 shows a cross-sectional view along the line XI—XI of FIG. 1.

FIG. 12 shows a side view of the attachment illustrated in FIG. 4.

SPECIFIC DESCRIPTION OF THE PREFERRED EMBODIMENT

Figure 8:
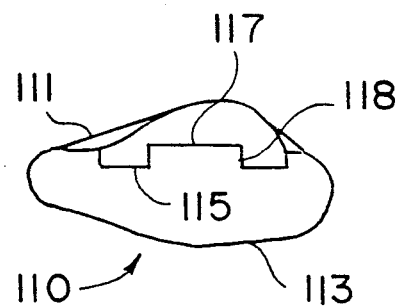
FIG. 8 shows a cross-sectional view along the line VIII—VIII of FIG. 7.

With reference first to FIGS. 1-4, a patellar clamp-guide device is generally designated by the reference numeral 10 and is seen to include a first handle 11 and a second handle 13, which handles are attached together at a fulcrum 15 by virtue of a bolt 17 extending through an opening 19 in the handle 13 and having a threaded end 21 threadably received in a threaded opening 23 in the handle 11. These details are best seen with reference to FIG. 2.

A locking device 25 is mounted on a proximal end of the handle 11 at a pivoting connection 27 and extends through an opening 29 formed in a proximal end of the handle 13. The locking device 25 includes a threaded rod 31 extending through the opening 29 as described above and having a threaded fastener 33 threaded thereover and engageable with an outside surface 14 of the handle 13 to lock the position of the handles 11 and 13 with respect to one another as desired. A leaf spring 35 is pivotably engaged to the handle 11 at 37 and is fastened to the handle 13 preferably by fastening devices such as the screws 39 shown in FIG. 1. Other fastening devices may be selectively employed.

The distal end of the handle 11 includes a projecting portion 12 in which the opening 21 is formed, an extension 41 carrying a guiding sleeve 43 and a curved portion 45 terminating at a flat surface 47 on which is mounted a patella engaging plate 49 having a plurality of upstanding spikes 51 designed to enter the anterior surface of the patella in use. A patella is shown in FIG. 1 prior to entry of spikes 51 therein. While a plurality of spikes 51 is preferred, if desired, a single spike with peripheral ribs (not shown) to prevent relative rotation between the plate 49 and patella could be employed.

The guiding sleeve 43 is designed to guidingly receive a plunger 53 having a slot 55 at one end thereof designed to receive a protrusion 57 forming a termination of an elongated portion 56 of the handle 13 distal of the fulcrum 15. Thus, movements of the handle 13 with respect to the handle 11 cause reciprocatory movements of the plunger 53 within the guiding sleeve 43.

The plunger device 53 has an end 59 remote from the slot 55 which end includes a blind threaded bore 61 sized to receive the threaded end 60 of a locking fastener 63, which locking fastener 63 also includes a knurled hand gripping portion 65 designed to be gripped by the user so that the locking fastener 63 may be rotated in one or the other direction.

As best seen with reference to FIGS. 1 and 3, a reamer guide 70 is detachably connected to the plunger 53 by virtue of the locking fastener 63. As seen in FIG. 3, the reamer guide 70 includes an attachment portion 71 having an elongated slot 73 therein, and a guide portion 75 having a central guiding opening 77 as well as an outer periphery 79 substantially concentric thereto. FIG. 3 shows a preferred alignment of the opening 77 over a patella.

As should be understood by those skilled in the art, with further reference to FIGS. 1 and 3, loosening of the locking fastener 63 allows sliding movement of the reamer guide 70 as the slot 73 may be moved with respect to the fastener device 63 when it is loosened with respect to the plunger 53. Thus, different sized reamer guides 70 may be assembled to the plunger 53 to fit different sized patellae. In the preferred embodiment of the present invention, between the extension 41 and the curved portion 45, a guide structure 46 is provided which may be engaged with the proximal end 72 of the slot 73 to provide guidance to the reamer guide in its reciprocatory movements along with the plunger 53. This relationship is seen with reference to FIG. 11 which illustrates the above-described relationship. The depth of the reamed hole is controlled by the reamer guide 70 articulating edges 76 striking the patella articular surface 111. The reaming cutter device 100 extends a prescribed distance past these edges 76 until it stops by engagement of the shoulder 129 of the reaming cutter device 100 on top surfaces of opening 77. This procedure ensures a precise depth of reamed bone regardless of the patellar height provided there is enough bone stock to ream.

With particular reference to FIGS. 3 and 4, a drill guide 80 may be added to the reamer guide 70 where it is desired to form small holes as desired in a patellar surface for recessing the fixation pegs of the patellar prosthesis. Thus, the drill guide 80 includes a locator pin 81 designed to engage at the slot 78 of the cutter guide 70 as best seen in FIG. 3. The drill guide 80 includes a plate 83 having a central opening 85 as well as peripheral openings 87 each of which may suitably guide a drilling device. As best seen in FIG. 12, the drill guide 80 has a sleeve-like portion 89 having an outer periphery sized and configured to be slideably received within the opening 77 formed in the reamer guide, with the locator pin 81 inserted within the slot 78 of the reamer guide to prevent relative rotation.

Figure 6:
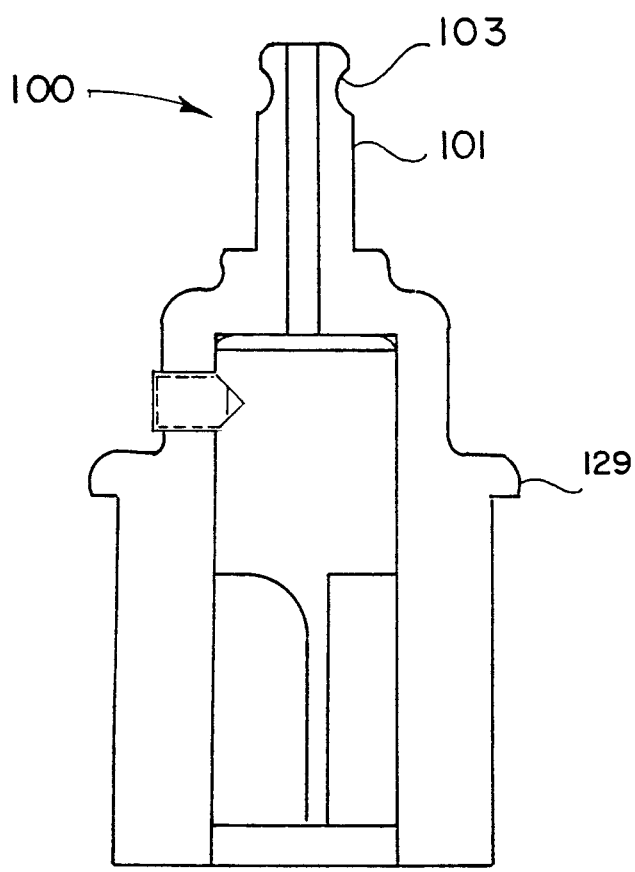
FIG. 6 shows a cross-sectional view along the line VI—VI of FIG. 5.
Figure 5:
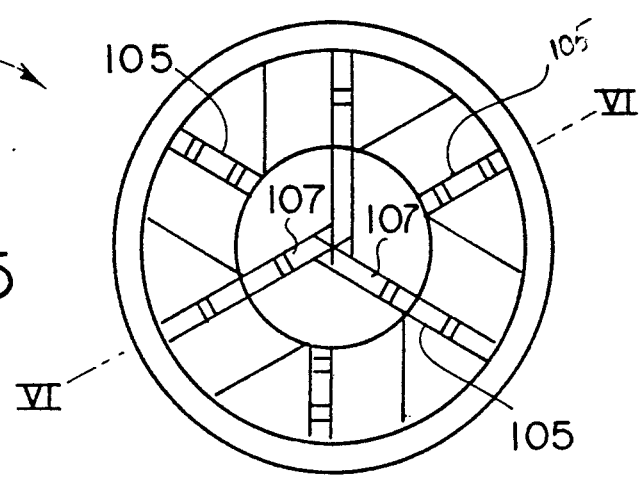
FIG. 5 shows an end view of the reaming cutter device of the present invention.

With reference, now, to FIGS. 5 and 6, a reaming cutter device is generally designated by the reference numeral 100 and is seen to include a chuck 101 having an annular recess 103 adapted to couple with an annular protrusion formed on interior surfaces of a coupling device for a rotary machine (not shown). With the chuck 101 coupled to the rotary machine (not shown), the reaming cutter device 100 may be rotated so that reaming operations may be carried out.

With reference to FIG. 5, the reaming cutter device 100 includes peripheral cutters 105 surrounding central cutters 107. With reference to FIG. 6, it is seen that the cutters 105 extend outwardly from the chuck 101 a further distance than the central cutters 107, thus, forming a stepped configuration as best seen in FIG. 6. If desired, the surfaces of the cutters 105, 107 as well as the inner bearing surfaces of the opening 77 of the cutter guide 70 may be coated with a gall resistant coating such as BKAZOL TM, a coating made preferably from a mixture of 80% NICOBRAZ 50 and 20% NICROBRAZ 135. NICROBRAZ 50 is a brazing alloy powder which consists of, by weight, 14% Chromium, 0.1% Silicon, 0.2% Iron, 10% Phosphorous and the balance Nickel. NICROBRAZ 135 is also a brazing alloy powder which consists of, by weight, 3.5% Silicon, 1.9% Boron, 1.5% Iron and the balance Nickel.

With reference to FIGS. 7 and 8, it is seen that the patella 110 includes an articular surface 111 and an anterior surface 113. Through the use of the inventive reamer 100, the articular surface 111 of the patella 110 is reamed to form a stepped surface including an annular surface 115 formed by the cutters 105 and a central raised bony surface 117 formed by the cutters 107.

Figure 9:
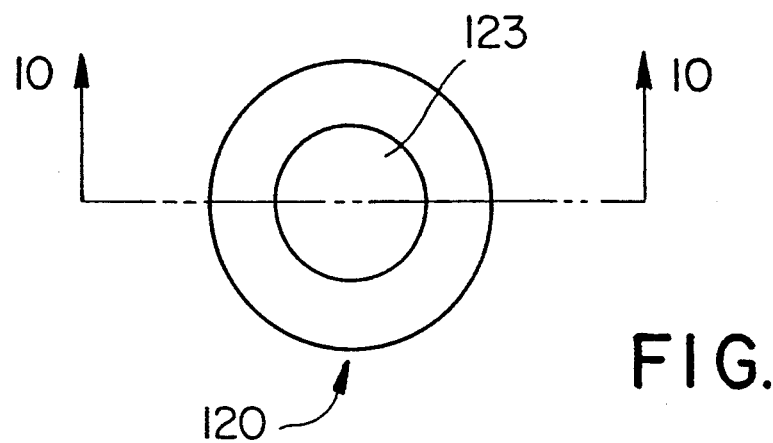
FIG. 9 shows a bottom view of a patellar button prosthesis.
Figure 10:
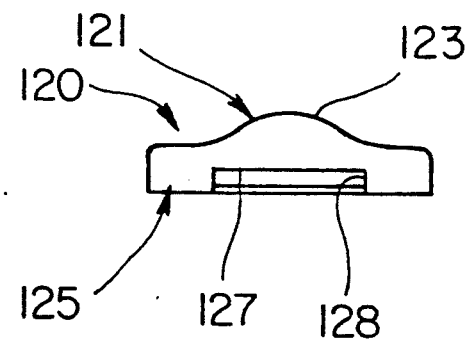
FIG. 10 shows a cross-sectional view along the line X—X of FIG. 9.

With reference to FIGS. 9 and 10, a patellar button prosthesis 120 is seen to include an articular surface 121 having a central raised portion 123, and a posterior surface 125 having a central recess 127. When the patellar button prosthesis 120 is installed on a patella 110 which has been reamed using the reamer 100 in accordance with the teachings of the present invention, the recess 127 thereof is sized and configured to snugly fit over and surrounding the surface 117 which has been reamed by the cutters 107 of the reaming cutter device 100. The surface 117 terminates at shoulder 118 which is sized and configured to engage the sidewalls 128 of the recess 127 in the posterior side 125 of the patellar button prosthesis 120.

Referring back to FIGS. 1 and 2, the inventive device 10 includes stop means. It is seen that the plunger 53 has extending outwardly therefrom a stop pin 54 which is sized and configured to engage a top surface 44 of the guide sleeve 43 of the handle 11 when the handles 11 and 13 are squeezed together a prescribed distance. As the handles 11 and 13 are so squeezed together, the plunger 53 advances thus advancing the cutter guide 70 toward the plate 49 as seen in FIG. 1. When the cutter guide 70 has advanced toward the plate 49 a prescribed distance, the stop pin 54 will engage the surface 44 of the guide sleeve 43 to prevent further advancement of the cutter guide 70.

In circumstances where the patella 110 is sufficiently thick enough that reaming is possible and appropriate, the surfaces 76 of the guide sleeve 75 will engage the articular surface 111 of the patella 110 before the stop pin 54 can engage the surface 44 of the guide sleeve 43. Under such circumstances, the surgeon will know that it is possible and feasible to ream the anterior surface 111 of the patella 110 to provide an attachment surface for the patellar button prosthesis 120.

On the other hand, should the stop pin 54 engage the surface 44 prior to engagement of the surfaces 76 of the cutter guide 70 with the anterior surface 111 of the patella 110, this will tell the surgeon that the patella 110 is not sufficiently thick enough to facilitate safe reaming thereof, since reaming thereof will remove too much of the bone of the patella to make fixation of a patellar button prosthesis 120 feasible. Such reaming would damage the structural integrity of the patella 110 sufficiently to compromise long-term results.

Thus, the position of the stop pin 54 with respect to the surface 44 taking into account the position of the surface 76 of the cutter guide 70 is specifically designed so that the surgeon has an automatic protection against accidentally reaming a patella which is not suitable for reaming. Thus, the surgeon knows that if the patellar clamp-guide device 10 is firmly clamped on the anterior and posterior surfaces of the patella, with the stop pin 54 spaced from the surface 44, safe reaming may take place. Should the patellar clamp-guide device only be engaging the patella 110 from the anterior side thereof by virtue of the spikes 51, then the surgeon knows that safe reaming may not take place. Thus, the inventive patella clamp-guide device 10 has a built-in safety feature.

In the method of performing surgery using the patella clamp-guide device 10 and the reaming cutter device 100, the following procedure is preferably carried out:

(1) An incision is made by the surgeon on the knee in such a manner so as to expose the patella and the adjacent knee structure to view.

(2) Other aspects of the surgery may be carried out by the surgeon before or after work on the patella is performed, such aspects including installation of a distal femoral prosthesis and installation of a proximal tibial prosthesis. When operating on the patella, the surgeon may take peripheral and thickness measurements thereof to ascertain the particular dimensions of the patella in question so that a desired patellar button prosthesis 120 may be chosen.

(3) As should be understood by those skilled in the art, the reamer guide 70 is made to be interchangeable with reamer guides of differing sizes and configurations for differing sized patellae. With the reamer guide 70 installed on the patellar clamp-guide device 10 in the manner described above, the spikes 51 of the plate 49 are engaged centrally on the anterior surface of the patella 110 and the handles 11, 13 are squeezed together until the surfaces 76 of the reamer guide 70 engage the articular surfaces of the patella 110. The plurality of spikes 51 are provided to prevent relative rotation of the patella 110 and device 10. In an important aspect of the surgery, the central ridge 112 (see FIGS. 1, 3 and 7) of the patella 110 is used as an anatomical landmark to properly align the reamer guide 70 thereover. As is known by those skilled in the art, the central ridge 112 of the patella 110 is not in and of itself a bearing surface. The actual bearing surfaces on the patella 110 are two surfaces spaced laterally to each side of the central ridge 112. Thus, the central ridge 112 may be used as an anatomical landmark since the surgeon knows that the bearing surfaces of the patella will be closely spaced to either side thereof. The central ridge 112 is located medially off center of the patellar articular surface 111 as best shown in FIG. 3. The inventive device compensates for this anatomical fact by using an anatomical algorithm generated curved surface 128 to match the articular surface 111 for each sized patella. This mechanical feature allows for a more precise fit of the reamer guide 70 onto the articular surface 111 of the patella. It also correctly locates the anatomical center of the patellar articular surface 111 which is important when installing a patellar prosthesis 120 that mimics the normal anatomical ridge 112. It is well known that rotational malalignment of this ridge severely compromises long term results. The anatomically derived algorithm curve 128 also allows for the edges 76 of the reamer guide 70 to abut the patella before striking the patellar ridge 112 thus leveling the patella in the instrument while being clamped.

The complex curve, comprising the curved surface 128, which is necessary to fit the articular surface of the patella became apparent to Applicant when studying the complex articular surfaces of cadaver specimens. Several observations from these studies were:

a) The central ridge of the patella is off center medially.

b) The central ridge height is fairly constant regardless of patella size.

c) The central ridge runs along the longitudinal axis of the patella.

d) The width of the articular surface of the patella is, generally speaking, about 25% larger than the length.

e) The curve on the medial side of the articular surface is fairly abrupt compared to the flat curve on the lateral side thereof.

Applicant has concluded from these observations that:

1) The reamer surface should be displaced medially because the functional center of the patellar mechanism follows the central ridge.

2) Peak of the ridge can be constant.

3) The reamer should be aligned about 90° to the longitudinal axis of this ridge to properly align the patellar-femoral mechanism.

4) Centering the reamer on the visible available articular bone is frequently incorrect.

5) A centered radius will not work.

Applicant consequently decided to use the anatomical ridge of the patella as a centering landmark to properly align the patellar prosthesis.

The following method was used to determine this complex curve: Referring to FIG. 1, the best fitting radial curve was found from the center of the patellar ridge to the outer medial edge of the reamer. This was done by analyzing a computer tomography (C.T.) data base of various sized patellae and by making templates that fit over the patellar articular surface. These curve radii were established for each size of articular surface. The sizes were determined by analyzing a data base of over 220 patellae measured from cadavers and surgical measurements. Once the radius of the curve was established in this manner, the algorithm for the complex curve was determined by drawing the proper sized opening of the reamer guide, then measuring up the standard height H of the ridge when the predetermined radius R is tangent to the lower outer edge 76a of the reamer point M and tangent to line H. This establishes the center location of the radius center point C. Since the center point C is spaced medially, the lateral segment LS of the curve is completed by drawing a line from the lower outer lateral edge 76b of the reamer guide point L tangent to the circle created from center point C. The composite curve thus created comprises a patella engaging surface which best fits the articular surface for that particular sized patella and prevents tilting, juggling or pivoting movements of said reamer guide when engaging said articular surface. The curve is parallel in the medial-lateral projection. The outer edges of the reamer guide, points M and L are the same length helping to level the patella when it is squeezed in the clamping device. As seen in FIG. 3, two such symmetric curved regions are provided on each reamer guide, with the respective terminations L, L and M, M being spaced from one another by the distance X in each case.

(4) If the surfaces 76 of the reamer guide 70 successfully engage the articular surface 111 of the patella 110, the surgeon knows, as explained above, that the patella 110 has sufficient thickness to allow proper and safe reaming while leaving enough patellar bone remaining to facilitate fixation of a patellar button prosthesis 120. Should the surfaces 76 of the reamer guide 70 not engage the articular surface 111 of the patella 110 or should they only partially engage the articular surface 111 of the patella 110, then the surgeon is advised not to ream the articular surface 111 of the patella as too much bony material will be removed therefrom.

(5) Assuming that the entirety of the surface 76 of the reamer guide 70 engages the anterior surface 111 of the patella 110 or substantially the entirety of the surface 76, the next step is to ream the articular surface 111 of the patella 110. For this purpose, the reaming cutter device 100 is attached to a rotary machine in a manner well known to those skilled in the art. Thereafter, the reaming cutter device 100 is inserted within the opening 77 of the reamer guide 70 and therethrough and into engagement with the articular surface 111 of the patella 110 so that surfaces such as those illustrated in FIGS. 7 and 8 may be formed thereon. The reaming cutter device 100 has a protruding lip 129 that stops on the superior surface of the reamer guide 70. This results in a uniform reamed depth regardless of the patellar size.

(6) Thereafter, a patellar button prosthesis 120 may be suitably installed on the articular surface 111 of the patella as reamed using a device such as, for example, the device illustrated in FIGS. 6 and 7 of the aforementioned prior U.S. Pat. Nos. 4,633,862 and 4,706,660.

As such, an invention has been disclosed in terms of a method of performing surgery and the instruments used in performing such surgery, which invention fulfills each and every one of the objects of the invention as set forth hereinabove and provides a new and improved surgical method incorporating the use of the instruments in an effective manner.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. A patellar clamp/guide device, comprising:
 a) a first handle having a proximal end and a distal end, and a second handle having a proximal end and a distal end, said handles being coupled together for mutual pivoting movement;
 b) said first handle distal end including:
  i) a plate having at least one upstanding spike adapted to engage an anterior surface of a patella; and
  ii) guide means for guiding a plunger in reciprocatory movements;
 c) said second handle distal end being coupled with said plunger whereby pivoting movements of said handles with respect to one another cause movements of said plunger with respect to said guide means;

d) a reamer guide removably attached to said plunger and including a guiding opening therethrough; and e) stop means for limiting spacing between said plate and said reamer guide to a desired minimum spacing.

2. The invention of claim 1, further including locking means interposed between said proximal ends of said handles for locking said handles in any one of a multiplicity of positions with respect to one another.

3. The invention of claim 1, further including biasing means interposed between said handles and biasing said proximal ends thereof away from one another.

4. The invention of claim 1, wherein said at least one upstanding spike comprises a plurality of spikes.

5. The invention of claim 1, wherein said guide means comprises a substantially cylindrical passage adapted to slidably receive said plunger.

6. The invention of claim 1, wherein said reamer guide has an anatomically derived algorithm curved surface which articulates with a corresponding articular surface of said patella to correctly center and level said reamer guide.

7. The invention of claim 1, further including a drill guide detachably mountable in said guiding opening.

8. The invention of claim 1, wherein said stop means comprises a protrusion on said plunger adapted to engage a surface on said guide means.

9. The invention of claim 8, wherein said protrusion comprises a pin.

10. The invention of claim 1, wherein said guiding opening guidingly receives a reaming cutter device adapted to ream a patellar button prosthesis receiving surface on an articular surface of said patella.

11. The invention of claim 10, wherein said reaming cutter device has stop means for limiting extent of movement thereof through said guiding opening to limit degree of reaming of said articular surface and provide a uniform depth of reamed bone surface.

12. The invention of claim 10, wherein said reaming cutter device includes first peripheral cutting blades and second central cutting blades.

13. The invention of claim 12, wherein said central blades are recessed with respect to said peripheral blades, whereby said patellar button prosthesis receiving surface is stepped with a central bony surface elevated with respect to a peripheral surface.

14. The invention of claim 12, wherein bearing surfaces of said guiding opening are coated with a gall-resistant coating.

15. A method of performing surgery including the steps of:

a) performing an incision exposing a patella;

b) engaging an anterior surface of said patella with a spiked plate;

c) moving a reamer guide connected to said plate toward an articular surface of said patella and aligning said reamer guide on said articular surface using a central ridge of said patella as an anatomical landmark to locate and align a proper plane of bone resection;

d) in the event said reamer guide engages said articular surface, using said reamer guide to guide a cutting device into engagement with said articular surface to ream said articular surface to form a stepped surface comprising a peripheral recessed surface and a central bony elevated surface; and e) installing a patellar button prosthesis on said reamed surface.

16. In a device for guiding reaming or drilling of an articular surface of a patella, the improvement comprising a patella engaging surface on said device adapted to engage said articular surface, said patella engaging surface having a curved portion merging into a straight portion and at least partially conforming to contours of said articular surface whereby firm engagement of said device on said articular surface may be accomplished and reaming or drilling may be carried out without relative movements between said device and patella.

17. The invention of claim 16, wherein said patella engaging surface comprises two symmetric regions.

18. The invention of claim 17, wherein said regions are spaced from one another.

19. The invention of claim 16, wherein said curved portion merges into said straight portion at a tangent point having an elevation on said device corresponding to a height of a patellar ridge.

20. The invention of claim 19, wherein said point is spaced medially with respect to a center of a guide opening of said device, said guide opening being peripherally defined by said patella engaging surface.

21. A patellar clamp/guide device, comprising:

a) a first handle having a proximal end and a distal end, and a second handle having a proximal end and a distal end, said handles being coupled together for movement with respect to one another;

b) said first handle distal end including:
  i) a plate having a surface thereon adapted to securely engage an anterior surface of a patella; and
  ii) guide means for guiding a plunger in reciprocatory movements;

c) said second handle distal end being coupled with said plunger whereby movements of said handles with respect to one another cause movements of said plunger with respect to said guide means; and d) a reamer guide removably attached to said plunger and including a guiding opening therethrough.

22. The invention of claim 21, further including stop means for limiting spacing between said plate and said reamer guide to a desired minimum spacing.

* * * * *